(12) United States Patent
Gellman et al.

(10) Patent No.: US 12,097,314 B2
(45) Date of Patent: Sep. 24, 2024

(54) VACUUM ASSISTED SKIN PENETRATING APPLIANCE WITH EXTERNAL INTERFACE

(71) Applicant: VIADERM LLC, Plymouth, MI (US)

(72) Inventors: Barry N. Gellman, Wilmington, DE (US); Kurt A. Dasse, Wilmington, DE (US); Allen B. Kantrowitz, Miami Beach, FL (US)

(73) Assignee: Viaderm LLC, Plymouth, MI (US)

( * ) Notice: Subject to any disclaimer, the term of this patent is extended or adjusted under 35 U.S.C. 154(b) by 1078 days.

(21) Appl. No.: 16/826,621

(22) Filed: Mar. 23, 2020

(65) Prior Publication Data

US 2020/0297905 A1    Sep. 24, 2020

Related U.S. Application Data

(60) Provisional application No. 62/822,673, filed on Mar. 22, 2019.

(51) Int. Cl.
| | |
|---|---|
| *A61M 1/00* | (2006.01) |
| *A61F 13/05* | (2024.01) |
| *A61M 1/36* | (2006.01) |
| *A61M 39/02* | (2006.01) |
| *A61M 39/06* | (2006.01) |
| *A61F 13/00* | (2006.01) |

(52) U.S. Cl.
CPC ........... *A61M 1/3653* (2013.01); *A61F 13/05* (2024.01); *A61M 1/912* (2021.05); *A61M 39/0247* (2013.01); *A61M 39/06* (2013.01); *A61F 2013/00174* (2013.01); *A61F 2013/00182* (2013.01); *A61M 1/85* (2021.05); *A61M 2039/0291* (2013.01); *A61M 2039/0673* (2013.01)

(58) Field of Classification Search
CPC ................ A61M 1/3653; A61M 1/912; A61M 39/0247; A61M 39/06; A61M 1/85; A61M 2039/0291; A61M 2039/0673; A61M 1/285; A61F 13/00068; A61F 2013/00174; A61F 2013/00182; A61F 13/05
USPC ......................................... 604/543
See application file for complete search history.

(56) References Cited

U.S. PATENT DOCUMENTS

| | | | | |
|---|---|---|---|---|
| 4,106,001 A | * | 8/1978 | Mahoney ................ | A61F 13/42 340/573.5 |
| 6,142,982 A | * | 11/2000 | Hunt ....................... | A61M 1/82 604/313 |
| 6,458,109 B1 | * | 10/2002 | Henley ................... | A61M 1/77 604/289 |

(Continued)

*Primary Examiner* — Andrew J Mensh
(74) *Attorney, Agent, or Firm* — MaxGoLaw PLLC

(57) ABSTRACT

An external protective interface is provided for intravenous infusion lines, drive lines, vacuum lines, and monitoring lines for percutaneous access. The interface acts as an airtight seal in concert with a vacuum line to promote accelerated tissue healing to reduce and prevent infection at insertion sites for infusion lines, drive lines, and medical devices. The interface provides additional mechanical stability to an implanted tube or PAD or so as to speed healing around a semi-permanent implanted tube or PAD, as well as connection points for vacuum lines and at least one drive line for the insertion of medical devices. The dense fibroblast ingrowth encouraged by the interface acts to strengthen barriers to infection at the insertion site.

7 Claims, 8 Drawing Sheets

(56) References Cited

U.S. PATENT DOCUMENTS

| | | | |
|---|---|---|---|
| 8,377,017 B2* | 2/2013 | Wilkes | A61F 13/0263 |
| | | | 604/304 |
| 2007/0118096 A1* | 5/2007 | Smith | A61M 1/94 |
| | | | 604/541 |
| 2014/0066868 A1* | 3/2014 | Freedman | A61M 37/00 |
| | | | 604/319 |
| 2017/0020737 A1* | 1/2017 | Zamierowski | A61F 13/05 |
| 2018/0043069 A1* | 2/2018 | Subilski | A61M 39/0247 |

* cited by examiner

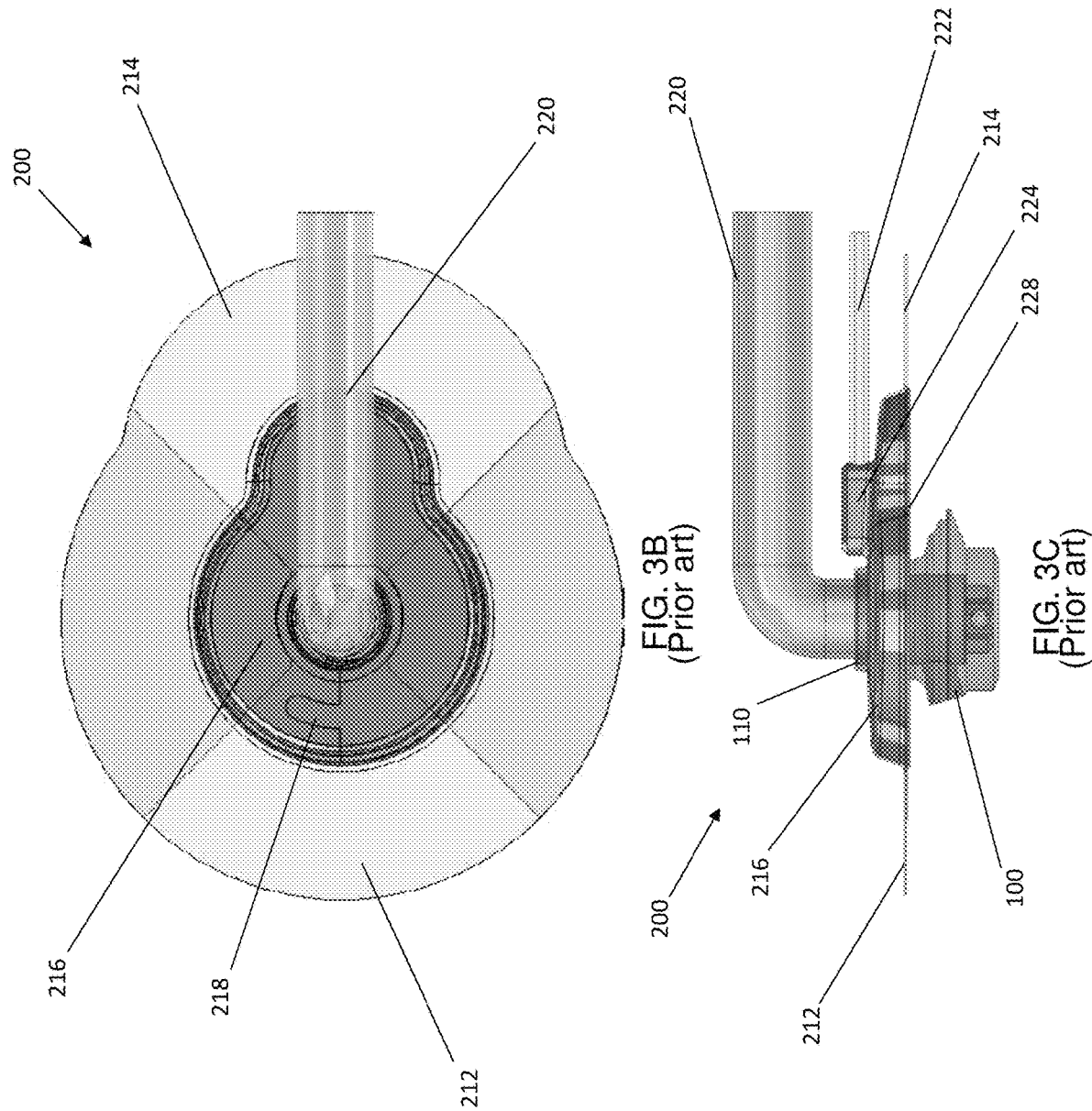

VACUUM ASSISTED SKIN PENETRATING APPLIANCE WITH EXTERNAL INTERFACE

RELATED APPLICATIONS

This application claims priority benefit of U.S. Provisional Application Ser. No. 62/822,673 filed 22 Mar. 2019, the contents of which are hereby incorporated by reference.

FIELD OF THE INVENTION

The present invention in general relates to medical devices and systems and in particular to a protective external interface for preventing infection at insertion sites of indwelling medical lines.

BACKGROUND OF THE INVENTION

In patients requiring long-term intravenous (IV) drug therapy, total parenteral nutrition, temporary access for kidney dialysis, or frequent blood testing, repeated access to a vein may be necessary over an extended period of time. Multiple needle sticks into a vein can be difficult, painful, and time-consuming. In such cases, a thin, flexible tube system known as a central venous catheter (also called a central line) may be inserted under the skin and into a large vein. This type of catheter may be safely and comfortably left in place for percutaneous access for days, weeks, or months. Additionally, peripherally inserted central catheters (PICC), skeletal guide wires, cardiac assist device lines, or other instruments may be kept in place for weeks or months with a precutaneous access device (PAD).

A common problem associated with implantation of a cutaneous access device (PAD) or other skin penetrating appliance is skin regeneration about the periphery of the appliance to form an immunoprotective seal against infection. New cell growth and maintenance is typically frustrated by the considerable mechanical forces exerted on the interfacial layer of cells. In order to facilitate skin regeneration about the exterior of the appliance, subject cells are often harvested and grown in culture onto appliance surfaces for several days prior to implantation in order to allow an interfacial cell layer to colonize appliance surfaces in advance of implantation. Unfortunately, cell culturing has met with limited acceptance owing to the need for a cell harvesting surgical procedure preceding the implantation procedure. Additionally, maintaining tissue culture integrity is also a complex and time-consuming task.

A related context in which cell growth is needed is wound healing, with DACRON® based random felt meshes have been used to promote cell regrowth in the vicinity of a wound, such felts have uncontrolled pore sizes that harbor bacterial growth pockets.

U.S. Pat. 7,704,225 to Kantrowitz solves many of these aforementioned problems by providing cell channeling contours, porous biodegradable polymers and the application of vacuum to promote cellular growth towards the surface the neck of a PAD. The facilitating of rapid cellular colonization of a PAD neck allows the subject to act as their own cell culture facility and as such affords more rapid stabilization of the PAD, and lower incidence of separation and infection.

FIG. 1A illustrates existing wound dressing 3 for prevention of infection at skin entry insertion sites of a catheter 1. FIG. 1B is a cutaway side view of the catheter 1 of FIG. 1A showing the skin layers and the insertion site 5. As noted the configuration shown in FIGS. 1A and 1B for catheters is prone to infection. Furthermore, as previously noted pulling of the catheter 1 and the considerable mechanical forces exerted on the interfacial layer of cells frustrates the healing process and makes the patient susceptible to infection at the insertion site.

FIG. 2 depicts a PAD generally at 100 as shown in U.S. application Ser. No. 13/416,546 to Kantrowitz. A cap 102 is formed of a material such as silicone, a polymer, or a metal and serves to keep debris from entering the device 100. Preferably, the cap 102 is remote from the surface of the epidermis E. The medical appliance 34 depicted as a catheter and vacuum or hydrodynamic draw tubing 104 pass through complementary openings 106 and 108, respectively formed in the cap 102. The tubing 104 provides fluid communication between a vacuum or hydrodynamic draw source 22 and an inner sleeve 12*d*. The inner sleeve 12*d* is characterized by a large and rigid pore matrix 18 in fluid communication to a vacuum source 22 such that the source 22 draws (arrow 22D) tissue fluid and fibroblasts 21 into the sleeve 12*d*. Sleeve 12*d* has a surface 24 that is optionally nanotextured to promote fibroblast adhesion. The surface 24 is optionally decorated with a pattern of contoured cell-conveying channels. It is appreciated that inner sleeve 12*d* optionally includes matrix 26 thereover, a coating substance 27, or a combination thereof. The coating 27 is appreciated to need not cover the entire surface 24. The tissue contacting surface 29 of substance 27 is optionally nanotextured. A flange 112 is provided to stabilize the implanted device 100 within the subcuteanous layer S. A flange 112 is constructed from materials and formed by methods conventional to the art. For example, those detailed in U.S. Pat. Nos. 4,634,422; 4,668,222; 5,059,186; 5,120,313; 5,250,025; 5,814,058; 5,997,524; and 6,503,228.

U.S. application Ser. No. 15/555,952 assigned to the assignee of this application discloses a modular external interface that includes a main body with an aperture configured to form a collar seal about an external neck portion of a skin penetrating appliance, such as the PAD 100 of FIG. 2, where a slit extends outward from the aperture. A portal is configured for insertion of a vacuum tube is on the main body, where the portal is in fluid communication with a vacuum channel on a bottom side of the main body. A foam layer is positioned under the main body, and at least one driveline inserted through the aperture and into the appliance. The modular external interface provides additional mechanical stability to an implanted PAD so as to speed healing around a semi-permanent implanted PAD, as well as connection points for vacuum lines and at least one drive line for the insertion of medical devices.

FIGS. 3A-3C illustrate the aforementioned modular external interface housing 200 coupled to the PAD 100 of FIG. 2. The modular external interface 200 forms a collar about the neck 110 of the PAD 100 with the main body 216 with a locking feature 218, such as a male extension that engages a female receptacle or cavity as a mechanical overlap connection. In a specific embodiment the main body 216 is made of silicone. As best shown in FIG. 4, the collar seal between the main body 216 and the neck 110 of the PAD 100 forms a hermetic seal with a gasket 230, which in a specific embodiment is a flexible gasket integrated into the main body 216. In a specific embodiment the gasket 230 may be a floating gasket. The stabilization of the PAD 100 within the skin to form a germ-free barrier requires subject cells to grow onto the neck surfaces 16 of the PAD 100 adjacent to the subject's epidermis E. The neck surface region 16 is adapted to promote growth of autologous fibroblast cells thereon. A suitable exterior side surface substrate for fibroblast growth is a nanotextured polycarbonate (LEXAN®).

The modular external interface 200 is secured and sealed to an outer layer of a patient's skin with a medical dressing. In a specific embodiment the medical dressing is a preform patterned and shaped to conform to the exterior of the modular external interface 200. In a specific embodiment the medical dressing preform may be in two halves (212, 214) that overlap. In a specific embodiment the medical dressing preform may be transparent. In a specific embodiment the medical dressing preform may be made of Tegaderm™ manufactured by Minnesota Mining and Manufacturing Company.

The modular external interface 200 has a central opening adapted at least one drive line 220 for insertion into a PAD, and a portal 224 for a vacuum line 222. As best shown in FIG. 4 a skin protection layer 228 and a foam disc (not visible) are positioned in the interior of the modular external interface 200.

While there have been many advances in skin penetrating appliance designs for preventing infection at the site of skin access, there continues to be a need for improved external interfaces for implanted appliances. In particular, infection at insertion sites of short and long-term IV lines, chronic central venous access, catheters, peritoneal dialysis lines, heart and total heart assist device drive lines, and orthopedic (prosthetics osseo-integration) related applications continue to require new and innovative solutions for the acceleration of tissue healing at an insertion site.

Thus, there exists a need for improved and integrated solutions for accelerated tissue healing to reduce and prevent infection at insertion sites for infusion lines, drive lines, and medical devices.

SUMMARY OF THE INVENTION

An external protective interface is provided for percutaneous access. The external protective interface includes a cover defining a volume that encloses an insertion site of a percutaneous access device or tube, the cover having a lip about the perimeter of the cover, and a portal with a set of ports for insertion of a vacuum line and at least one driveline, the cover having an opening adapted to fit over the portal. A skin protection layer fits around the percutaneous access device and positions the portal against a subject's skin and helps to maintain a negative pressure against the surface of the patient's skin as supplied by the vacuum line, the lip resting on the skin protection layer. The external protective interface further includes a gasket that is adapted to conform to the shape of the lip and of the portal.

BRIEF DESCRIPTION OF THE DRAWINGS

The subject matter that is regarded as the invention is particularly pointed out and distinctly claimed in the claims at the conclusion of the specification. The foregoing and other objects, features, and advantages of the invention are apparent from the following detailed description taken in conjunction with the accompanying drawings in which:

FIGS. 3A-3C are prior art perspective views of a modular external interface seal for a PAD appliance;

DESCRIPTION OF THE INVENTION

The present invention is an external protective interface for intravenous infusion lines, drive lines, vacuum lines, and monitoring lines for percutaneous access. The external protective interface acts as an airtight seal in concert with a vacuum line to promote accelerated tissue healing to reduce and prevent infection at insertion sites for infusion lines, drive lines, and medical devices. Embodiments of the protective external interface provide additional mechanical stability to an implanted tube or PAD or so as to speed healing around a semi-permanent implanted tube or PAD, as well as connection points for vacuum lines and at least one drive line for the insertion of medical devices. The dense fibroblast ingrowth encouraged by embodiments of the invention acts to strengthen barriers to infection at the insertion site. Embodiments of the inventive external protective interface may be illustratively used for chronic central venous access, peritoneal dialysis, heart assist and total heart drivelines, prosthetics (osseo-integration—limb replacement), and short and long term IV access (reduction of bio-burden adjacent to non-adhering catheters).

While embodiments of the external protective interface is shown with a percutaneous tube, it is appreciated that it is applicable to a variety of such implant appliances including an embedded percutaneous access device (PAD), a catheter, a PICC line, an IV, a Steinman pin, and a Kirschner wire. Embodiments of the external protective interface provide for the hermaticity in the vicinity of the insertion site of the skin-appliance (PAD) interface with fluid exudate or transudate egressing from the vicinity of the skin-PAD interface via a vacuum or low pressure tube.

Figure 1A:
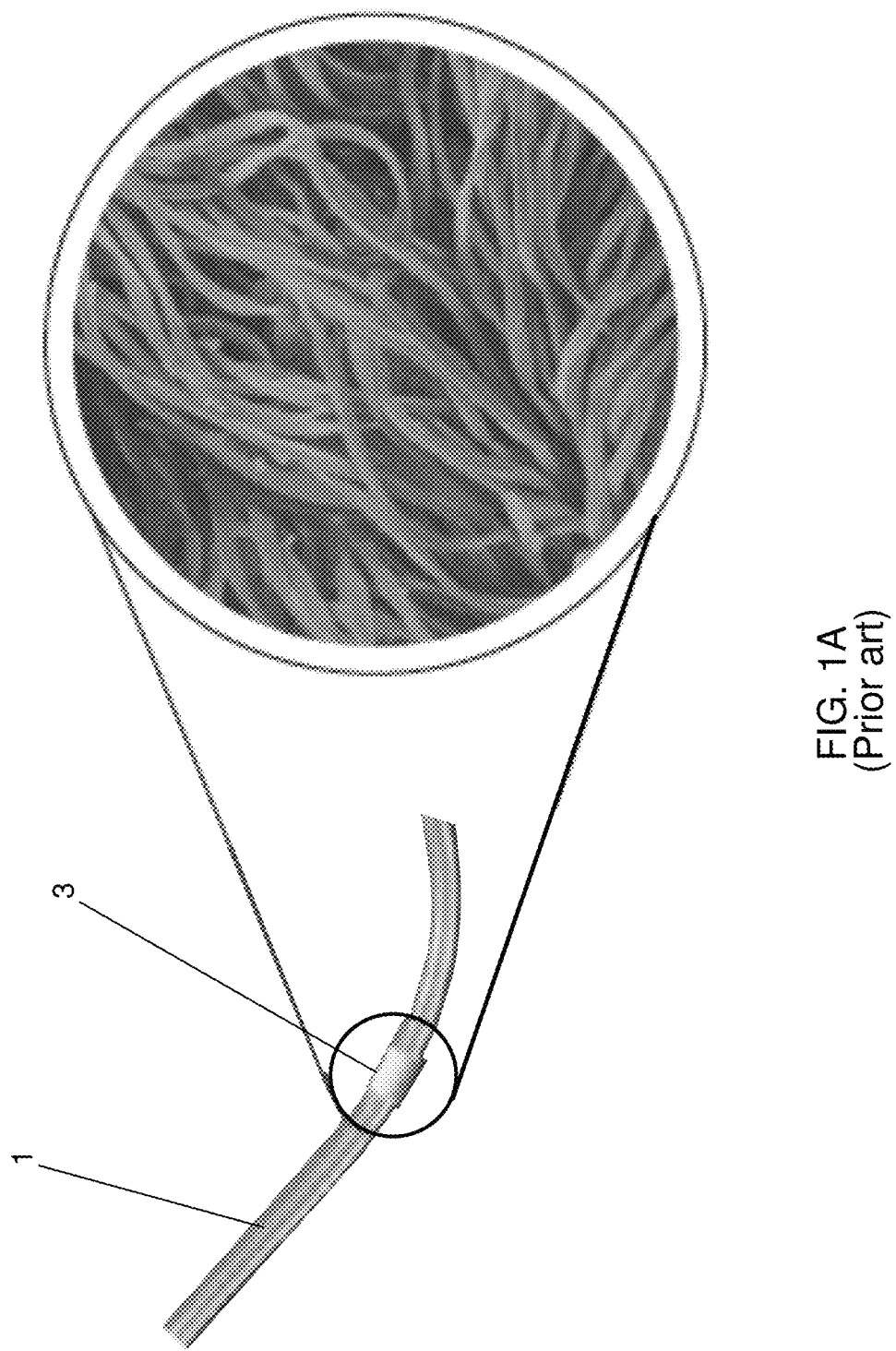
FIG. 1A illustrates existing wound dressing for prevention of infection at skin entry insertion sites of catheters.
Figure 1B:
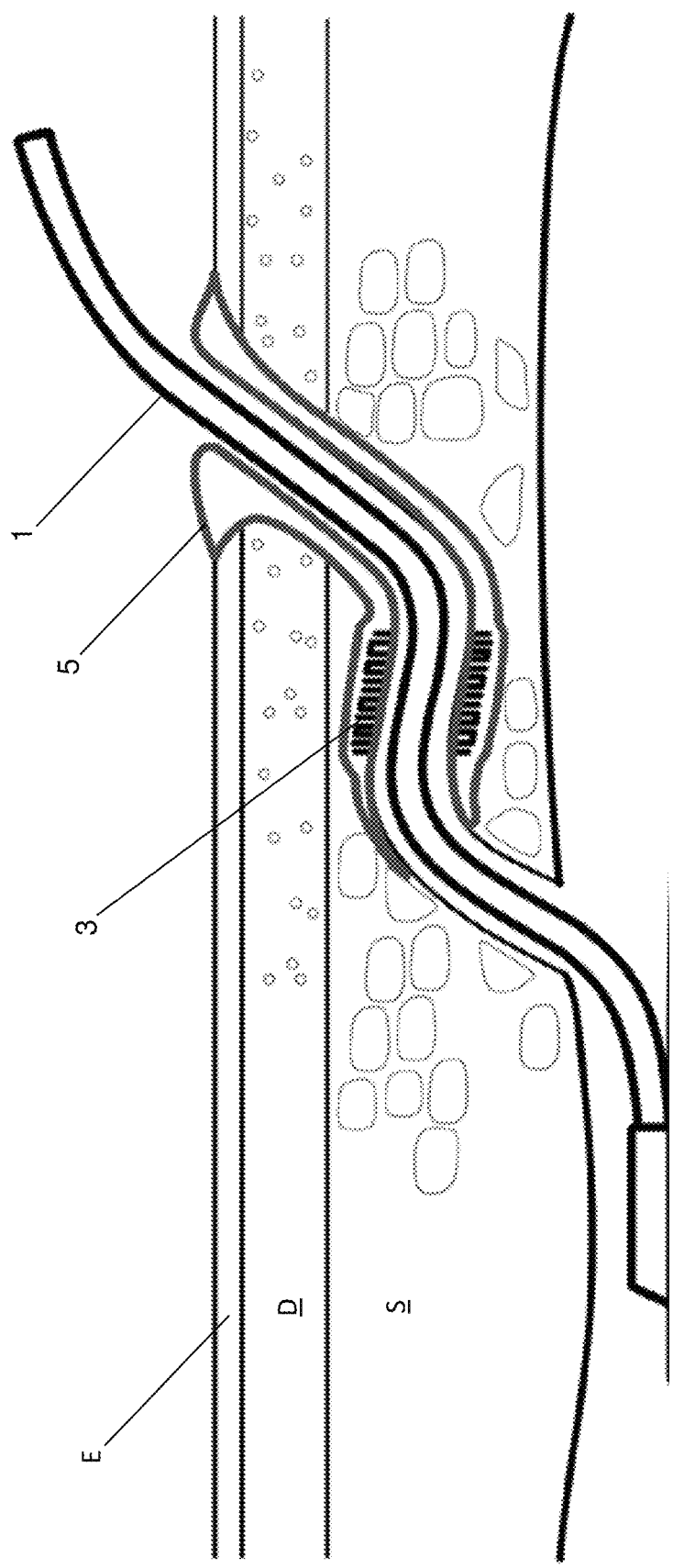
FIG. 1B is a cutaway side view of the catheter of FIG. 1A.
Figure 2:
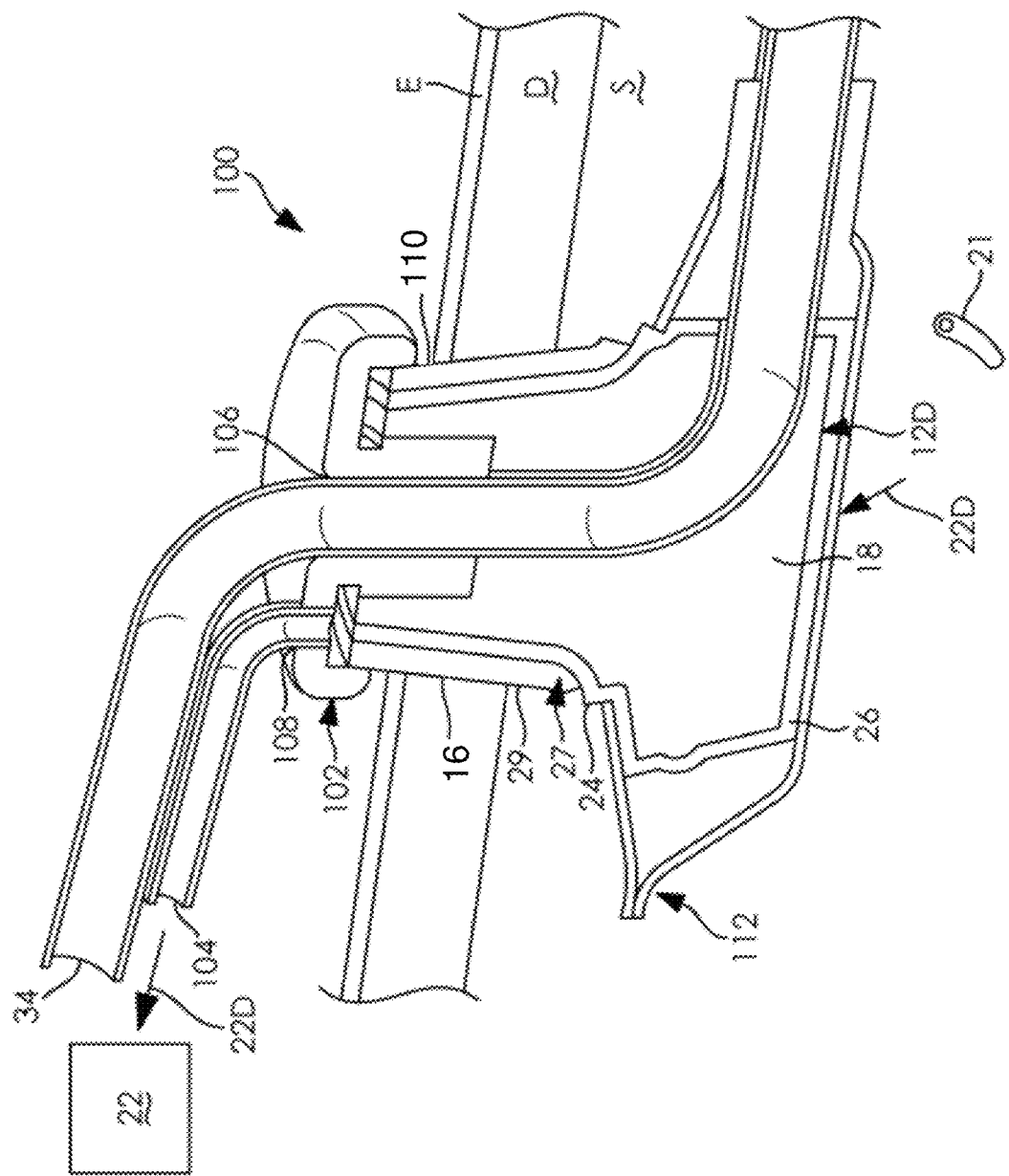
FIG. 2 is a prior art, partial cutaway view of a flanged percutaneous access device (PAD) with relative dimensions of aspect exaggerated for visual clarity.
Figure 3A:
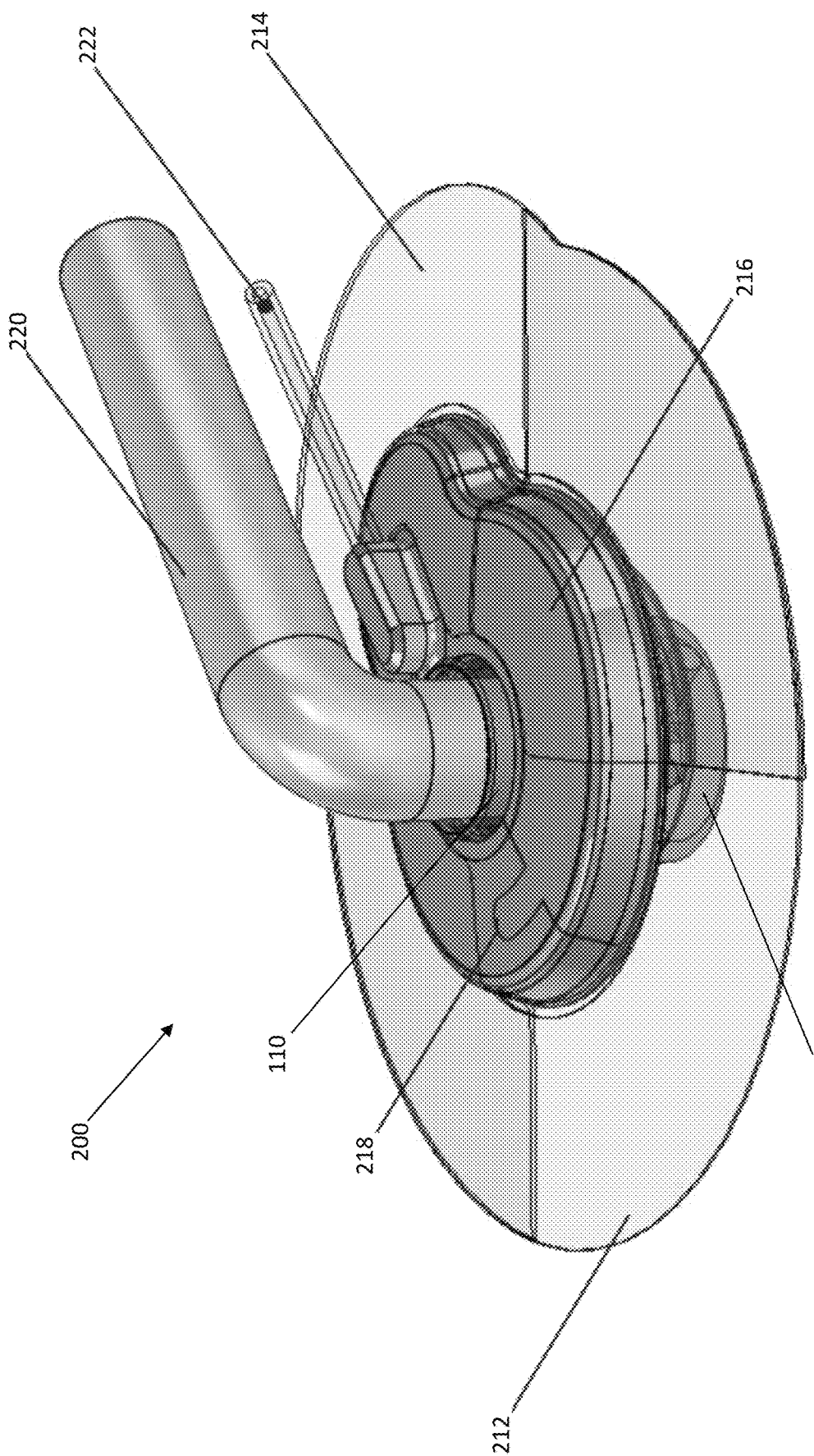
Figure 4:
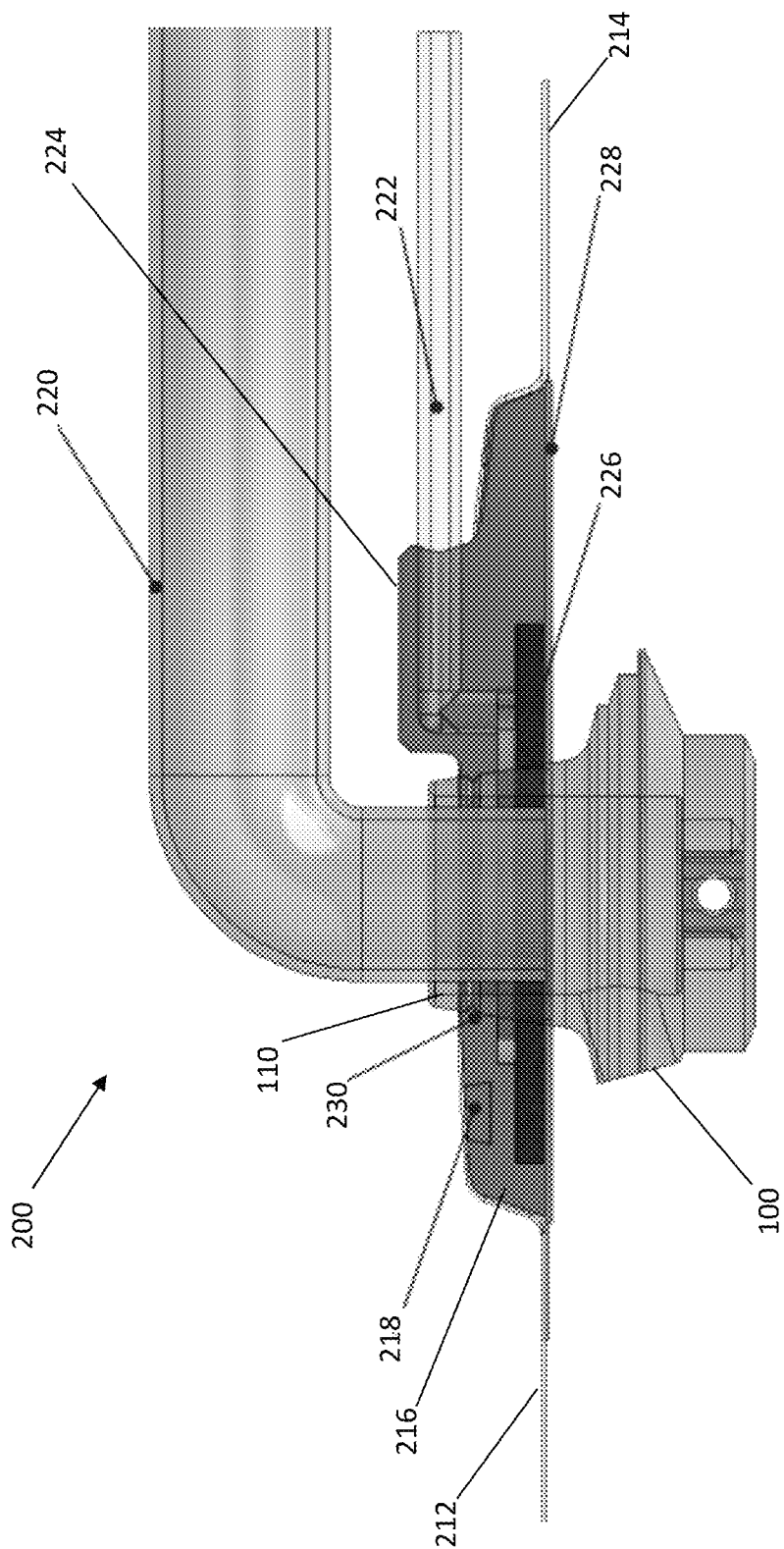
FIG. 4 illustrates a side cross sectional view of FIG. 3C.
Figure 5:
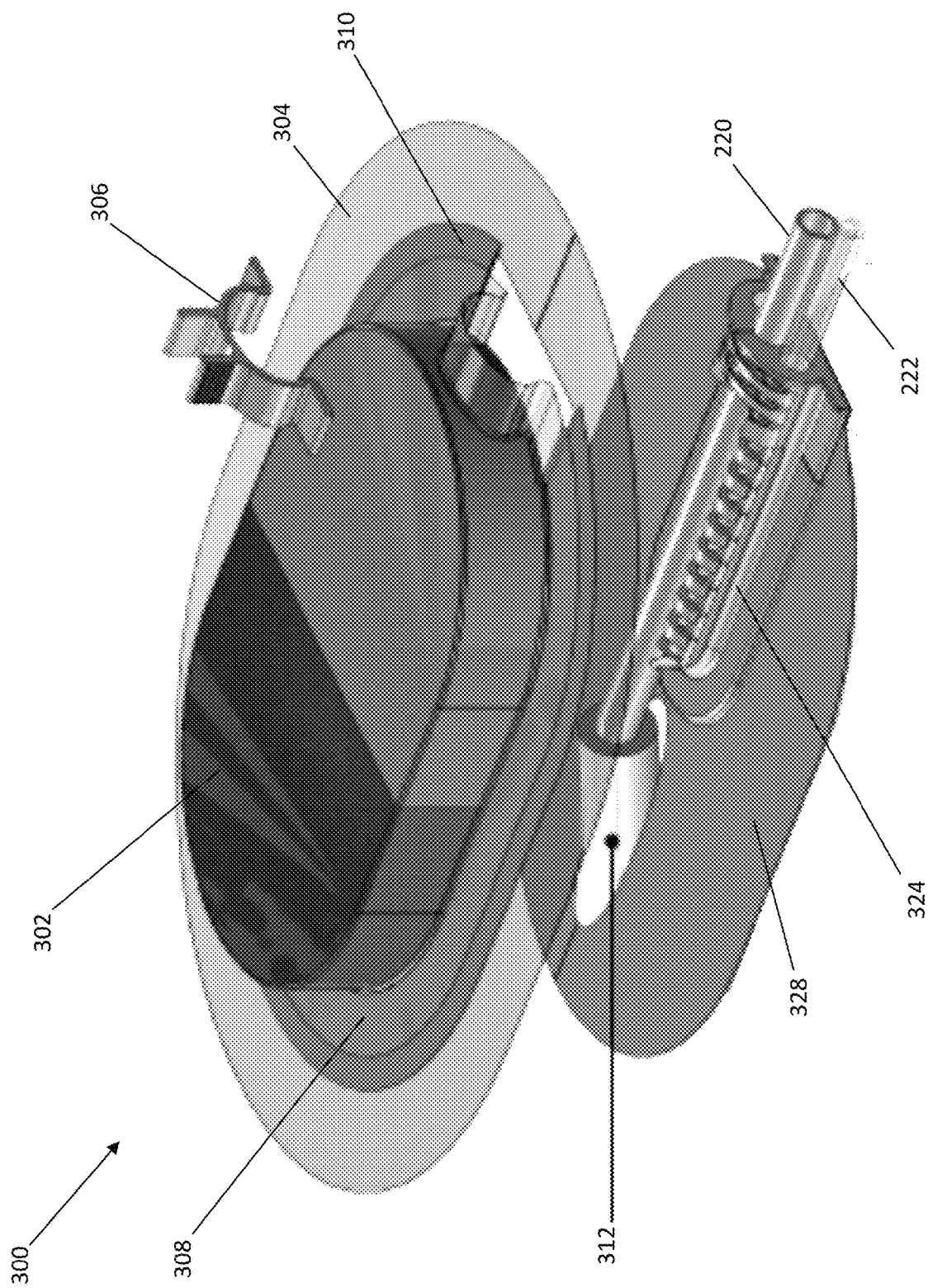
FIG. 5 is an exploded view of an external protective interface showing a dressing, cover, an implanted tube for an infusion or insertion line, and a vacuum line according to an embodiment of the invention.

Referring now to the figures, FIG. 5 illustrates an exploded view of an inventive embodiment of an external protective interface 300 with a cover 302 that fits over a portal 324, the portal having ports for insertion of a vacuum line 222 and at least one driveline 220 that is shown inserted into a percutaneous tube 312. The percutaneous tube 312 as disclosed in U.S. application Ser. No. 15/125,273 assigned to the assignee of this application has an exterior wall that is adapted to promote growth of autologous fibroblast cells thereon. A suitable exterior side surface substrate for fibroblast growth is a nanotextured polycarbonate (LEXAN®). In certain embodiments the exterior surface of the percutaneous tube 312 are etched by a laser or by a chemical treatment to obtain a surface finish or roughness to promote cell growth attachment to the exterior surface of the percutaneous tube 312. A skin protection layer 328 fits around the percutaneous tube 312 and positions the portal 324 against the skin and helps to maintain a negative pressure against the surface of the skin as supplied by the vacuum line 222. The portal 324 also supports the driveline 220 until the driveline 220 is inserted into the percutaneous tube 312. The modular external interface 300 and cover 302 is secured and sealed to an outer layer of a patient's skin with a medical dressing 304. In a specific embodiment the medical dressing is a preform 304 patterned and shaped to conform to a flexible gasket 308 and an exterior lip 310 of the cover 302 of the modular external interface 300. In a specific embodiment the medical dressing preform 304 may be transparent. In a specific embodiment the medical dressing preform 304 may be made of Tegaderm™ manufactured by Minnesota Mining and Manufacturing Company. Removable clip 306 seals the flexible gasket 308 to the portal 324 that provides a hermetic seal.

Figure 6:
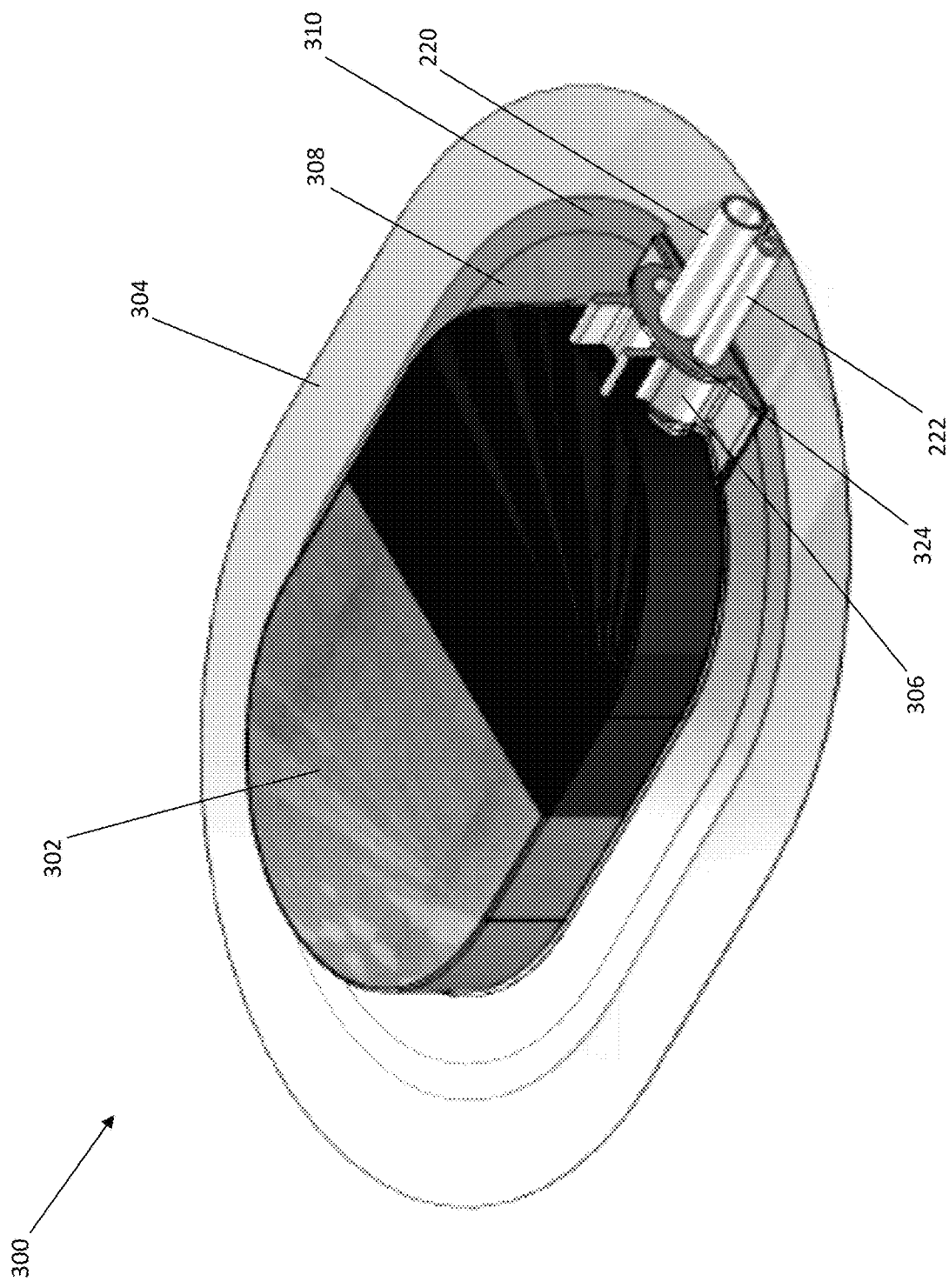
FIG. 6 illustrates the dressing applied to the external protective interface according to an embodiment of the invention.

FIG. 6 illustrates the dressing applied to the external protective interface 300 according to an embodiment of the invention with the vacuum line 222 and driveline 220 inserted to the portal 324.

The present invention is further detailed in the application appendix, the contents of which are hereby incorporated by reference.

Patent documents and publications mentioned in the specification are indicative of the levels of those skilled in the art to which the invention pertains. These documents and publications are incorporated herein by reference to the same extent as if each individual document or publication was specifically and individually incorporated herein by reference.

The foregoing description is illustrative of particular embodiments of the invention, but is not meant to be a limitation upon the practice thereof. The following claims, including all equivalents thereof, are intended to define the scope of the invention.

The invention claimed is:

1. An external protective interface for percutaneous access comprising:
   a cover having an upper portion lying in a first plane, a wall portion extending from a perimeter of the upper portion in a second plane that intersects the first plane, and a lip extending from a perimeter of the wall portion in a third plane that is parallel to the first plane, the upper portion of said cover and the wall portion of said cover defining a volume that encloses an insertion site of a percutaneous access device;
   a portal with a set of ports for insertion of a vacuum line and at least one driveline, said cover having a single opening at an end thereof in the wall portion adapted to fit over said portal and through which said vacuum line and said at least one driveline pass;
   a skin protection layer that fits around the percutaneous access device and positions said portal against skin of a subject and adapted to maintain a negative pressure against a surface of the skin as supplied by said vacuum line, said lip resting on said skin protection layer; and
   a gasket that is adapted to conform to the shape of said lip and of said portal.

2. The interface of claim 1, further comprising a clip that secures said gasket to said portal.

3. The interface of claim 1, further comprising a medical dressing for securing said cover to the patient's skin, wherein the medical dressing further secures said gasket to said lip.

4. The interface of claim 3, wherein said medical dressing is a preform.

5. The interface of claim 4, wherein said preform is transparent.

6. The interface of claim 1, wherein said portal supports said vacuum line and said at least one driveline until said at least one driveline is inserted in a percutaneous tube of the percutaneous access device.

7. A method of stabilizing a percutaneous access device comprising:
   implanting an interface according to claim 1 with the portal against skin of a subject;
   maintaining a negative pressure against the skin as supplied by the vacuum line, the lip resting on the skin protection layer.

* * * * *